(12) United States Patent
Glascott

(10) Patent No.: US 6,869,433 B2
(45) Date of Patent: Mar. 22, 2005

(54) POLYAXIAL SCREW WITH IMPROVED LOCKING

(75) Inventor: Craig Glascott, Hudson, OH (US)

(73) Assignee: Depuy Acromed, Inc., Raynham, MA (US)

( * ) Notice: Subject to any disclaimer, the term of this patent is extended or adjusted under 35 U.S.C. 154(b) by 48 days.

(21) Appl. No.: 10/043,550

(22) Filed: Jan. 11, 2002

(65) Prior Publication Data

US 2002/0151900 A1 Oct. 17, 2002

Related U.S. Application Data

(60) Provisional application No. 60/261,129, filed on Jan. 12, 2001.

(51) Int. Cl.[7] .............................................. A61B 17/70
(52) U.S. Cl. ............................ 606/73; 606/61; 606/72
(58) Field of Search .............................. 606/73, 53, 54, 606/60, 61, 65, 66, 72, 86, 87, 103, 69, 70, 71, 75

(56) References Cited

U.S. PATENT DOCUMENTS

| 5,024,213 A | 6/1991 | Asher et al. |
| 5,129,900 A | 7/1992 | Asher et al. |
| 5,312,404 A | 5/1994 | Asher et al. |
| 5,443,467 A | 8/1995 | Biedermann et al. |
| 5,681,319 A | 10/1997 | Juergen et al. |
| 5,743,907 A | 4/1998 | Asher et al. |
| 5,797,911 A | 8/1998 | Sherman |
| 5,885,286 A * | 3/1999 | Sherman et al. .............. 606/61 |
| 5,910,142 A * | 6/1999 | Tatar ............................ 606/61 |
| 6,022,350 A | 2/2000 | Ganem |
| 6,290,703 B1 | 9/2001 | Ganem |

FOREIGN PATENT DOCUMENTS

FR 2 748 387 A 11/1997

OTHER PUBLICATIONS

PCT International Search Report PCT/US02/00814 date of mailing Jul. 3, 2002.

* cited by examiner

Primary Examiner—Cary E. O'Connor
Assistant Examiner—Candice C. Melson
(74) Attorney, Agent, or Firm—Andrew C. Farmer

(57) ABSTRACT

A polyaxial pedicle screw assembly incorporates a concave portion on a receiver which mates with a convex surface on a head of the screw to form a ball joint. The radius of at least a portion of the concave surface is less than a radius of the mating convex portion whereby to create an interference fit.

8 Claims, 2 Drawing Sheets

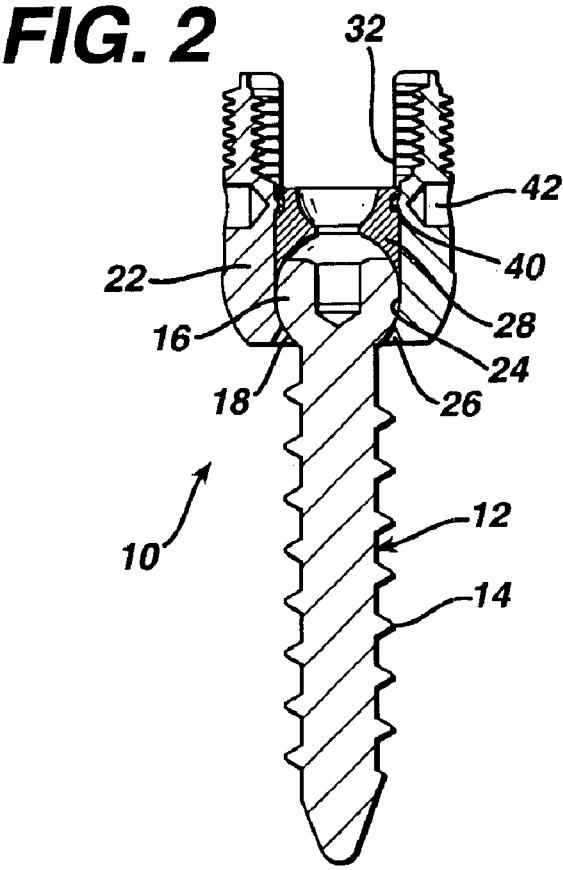
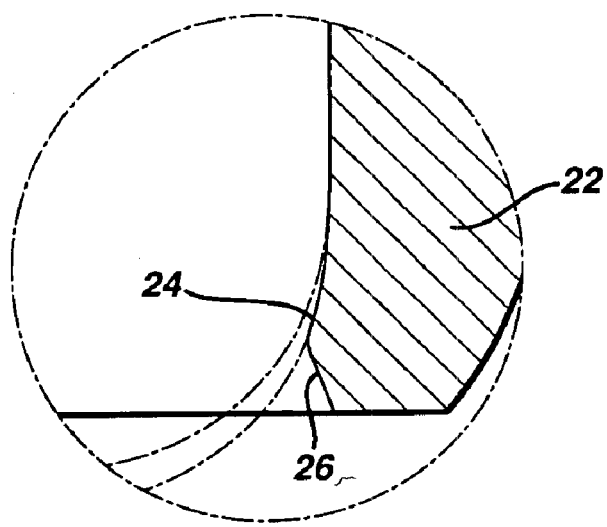

POLYAXIAL SCREW WITH IMPROVED LOCKING

This application claims priority from U.S. patent application Ser. No. 60/261,129 filed Jan. 12, 2001.

FIELD OF THE INVENTION

The present invention relates to a polyaxial pedicle screw.

BACKGROUND

Polyaxial pedicle screws such as disclosed in Biedermann et al.'s U.S. Pat. No. 5,443,467, incorporated herein by reference, are used for connecting vertebrae to rods in spinal surgery. They incorporate a ball joint at the connection to the rod to allow the surgeon some flexibility in placing the screws. Tightening a nut on the screw compresses the ball joint components to lock the angular position of the ball joint.

SUMMARY OF THE INVENTION

The present invention, improves the locking force achieved when locking the ball joint.

A pedicle screw assembly according to the present invention comprises a screw having a head with a convex portion and a receiver receiving the head. The receiver also receives an elongate member, such as a spinal fixation rod. The receiver has a concave portion which has a radius of curvature which is less than a radius of curvature of the convex portion of the head whereby to create an interference fit between the convex portion of the head and the concave portion of the receiver.

Preferably, a nut on the receiver compresses the convex portion of the head into the concave portion of the receiver. In one convenient orientation, the receiver comprises a U-shaped portion for receiving the elongated member. Preferably, the concave portion of the receiver is formed of titanium. Although other shapes may be employed, in one preferred orientation each of the concave portion and convex portion have a spherical shape. Any shapes which allow rotational freedom of the head and receiver prior to engagement of the surfaces would suffice.

In one preferred embodiment the screw comprises an elongated shank having bone threads thereon and the head located at one end thereof and the receiver comprises a body having an aperture therethrough for receiving the shank and having the concave portion located at the aperture. The receiver further comprises a channel therethrough opposite the aperture, the channel receiving the elongate member.

The pedicle screw can further comprises a compression member between the elongate member and the head; the head having a second convex portion facing the compression member and the compression member having a second concave portion facing the head, the second concave portion having a radius of curvature less than a radius of curvature of the second convex portion whereby to create an interference fit between the head and the pressure member.

The difference in the radius of curvature between the convex and concave portions in one embodiment is about 0.05 mm.

BRIEF DESCRIPTION OF THE DRAWINGS

FIG. 2 is an additional cutaway view of the screw of FIG. 1 with rod and locking nuts removed for clarity; and FIG. 3 is a detailed cutaway view of a portion of the receiver of FIG. 1.

DETAILED DESCRIPTION

Figure 1:
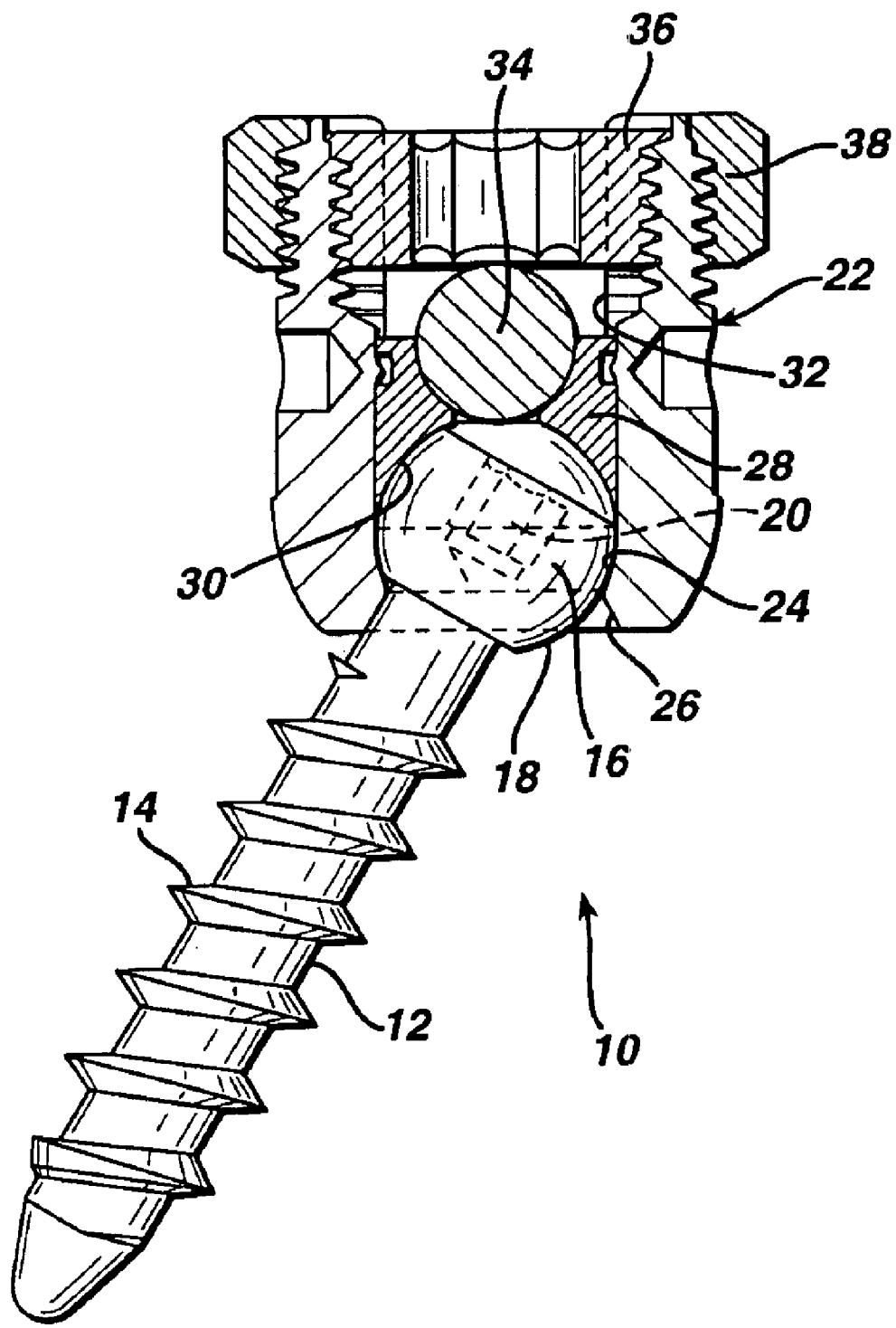
FIG. 1 is a cutaway view of a pedicle screw according to the present invention.

FIGS. 1 and 2 illustrates a polyaxial screw assembly 10 according to the present invention. It comprises a screw 12 having cancellous threads 14 for insertion into the cancellous bone of a vertebra, especially through the pedicle. A spherically shaped head 16 has a convex surface 18 and a tool recess 20 for receiving a hex driver or other tool (not shown). The head 16 is received within a tubular receiver 22 having an internal concave surface 24 and an adjacent opening 26. The convex surface 18 of the head 16 mates with the concave surface 24. The opening 26 is smaller than the head 16 so that the screw 12 can project out of the opening 26 without falling out of the receiver 22.

A pressure disk 28 sits atop the head 26 and has a surface 30 of mating shape to that of the head 26. The receiver also has a U-shaped portion 32 which receives an elongated rod 34. The rod 34 is used to connect adjoining vertebrae as is known in the art. An internal nut 36 and external nut 38 compress the rod 34 against the pressure disk 28 which in turn compresses the head convex portion 18 into the receiver concave portion 24 and locks the angular position of the receiver 22 with respect to the screw 12.

The pressure disk 28 preferably has a lateral indentation 40 into which a material on the receiver 22 is swaged 42 to hold the pressure disk 28 within the receiver 22 but allow some movement therein.

FIG. 3 illustrates the feature which improves the locking of the receiver 22 with respect to the screw 12 over prior similar screw assemblies. The concave surface 26 has a slightly smaller radius of curvature than does the convex surface 18 so that when the two are compressed together, the material deforms somewhat to allow the surfaces to mate in an interference fit and thus enhances the grip between the surfaces.

Tests of the deflection of the screw 12 under a torque load versus a prior screw show a significant decrease in deflection versus the prior screw, thus less slippage and better locking. Tables 1 and 2 show the results of tests of screws with and without the interference fit. The seven screws in table 1 were formed of stainless steel and the seven screws in Table 2 of titanium. The screws labeled Magnum contain the interference fit and the others did not. The screws are of similar dimensions; the numbers listed after the screw refer to the rod size. The tests consist of locking the screws to a uniform torque and then applying a lateral force to the screw 12 to induce a torque at the head 16. The load at an offset of 0.5 mm and the stiffness were assessed for each sample. The screws with the interference fit of the present invention exhibited gains in both parameters.

TABLE 1

Static Cantilever Beam Evaluation
Moss-Miami (no interference fit) vs.
Moss-Miami Magnum (interference fit)
Stainless Steel

| Specimen | 1 | 2 | 3 | 4 | 5 | 6 | 7 | Avg | Std Dev |
|---|---|---|---|---|---|---|---|---|---|
| Load at Offset 0.5 mm (Kn) | | | | | | | | | |
| Moss-Miami 6.0 | 0.2107 | 0.2188 | 0.2121 | 0.2926 | 0.2483 | 0.2349 | 0.3571 | 0.25 | 0.05 |
| Moss-Miami Magnum 6.34 | 0.2470 | 0.3101 | 0.3678 | 0.2752 | 0.2926 | 0.3074 | 0.2618 | 0.29 | 0.04 |
| Stiffness N/mm | | | | | | | | | |
| Moss-Miami 6.0 | 602.2 | 459.8 | 229.9 | 594.3 | 245.8 | 538.8 | 570.8 | 463.1 | 160.99 |
| Moss-Miami Magnum 6.34 | 637.0 | 705.2 | 627.8 | 611.4 | 753.2 | 721.1 | 689.8 | 677.9 | 53.27 |

TABLE 2

Static Cantilever Beam Evaluation Moss-Miami (no interference fit) vs.
Moss-Miami Magnum (interference fit) Titanium

| Specimen | 1 | 2 | 3 | 4 | 5 | 6 | 7 | Avg | Std Dev |
|---|---|---|---|---|---|---|---|---|---|
| Load at Offset 0.5 mm (Kn) | | | | | | | | | |
| Moss-Miami 6.0 | 0.2859 | 0.3047 | 0.2389 | 0.3074 | 0.2959 | 0.2403 | 0.3302 | 0.28 | 0.04 |
| Moss-Miami Magnum 6.34 | 0.3730 | 0.4495 | 0.4502 | 0.4929 | 0.5348 | 0.5342 | 0.5114 | 0.45 | 0.06 |
| Stiffness N/mm | | | | | | | | | |
| Moss-Miami 6.0 | 451.9 | 404.9 | 293.3 | 467.7 | 404.1 | 316.9 | 396.4 | 390.7 | 64.58 |
| Moss-Miami Magnum 6.34 | 707.4 | 572.1 | 573.9 | 526.6 | 580.0 | 578.7 | 517.1 | 584.5 | 58.38 |

In one preferred embodiment, the head convex surface 18 would have a diameter of 6.995 mm and the mating receiver concave surface 24 would have a diameter of 6.88 mm. Similar interference dimensions could also be applied to the mating interface of the pressure disk surface 30 and the head 16.

While the invention has been described with regard to a particular embodiment thereof, those skilled in the art will understand, of course, that the invention is not limited thereto since modifications can be made by those skilled in the art, particularly in light of the foregoing teachings. Reasonable variation and modification are possible within the foregoing disclosure of the invention without the departing from the spirit of the invention.

What is claimed is:

1. A pedicle screw assembly comprising:
   a screw having a head with a convex portion;
   a receiver receiving the head and an elongated member; and
   the receiver having a concave portion, the concave portion having a radius of curvature which is less than a radius of curvature of the convex portion of the head whereby to create an interference fit between the convex portion of the head and the concave portion of the receiver.

2. A pedicle screw assembly according to claim 1 and further comprising a nut on the receiver which compresses the convex portion of the head into the concave portion of the receiver.

3. A pedicle screw assembly according to claim 2 wherein the receiver comprises a U-shaped portion for receiving the elongated member.

4. A pedicle screw assembly according to claim 2 wherein the concave portion of the receiver is formed of titanium.

5. A pedicle screw assembly according to claim 1 wherein each of the concave portion and convex portion have a spherical shape.

6. A pedicle screw assembly according to claim 1 wherein the screw comprises an elongated shank having bone threads thereon and the head located at one end thereof;
   wherein the receiver comprises a body having an aperture therethrough for receiving the shank and having the concave portion located at the aperture;
   wherein the receiver further comprises a channel therethrough opposite the aperture, the channel receiving the elongate member.

7. A pedicle screw according to claim 6 and further comprising a compression member between the elongate member and the head; the head having a second convex portion facing the compression member and the compression member having a second concave portion facing the head, the second concave portion having a radius of curvature less than a radius of curvature of the second convex portion whereby to create an interference fit between the head and the compression member.

8. A pedicle screw according to claim 1 wherein the radius of curvature of the concave portion is about 0.05 mm smaller than the radius of curvature of the convex portion.

* * * * *